(12) United States Patent
Siess et al.

(10) Patent No.: US 12,397,147 B2
(45) Date of Patent: Aug. 26, 2025

(54) METHOD AND APPARATUS FOR CALIBRATION AND USE IN ESTIMATING BLOOD FLOW IN AN INTRAVASCULAR BLOOD PUMP

(71) Applicant: Abiomed Europe Gmbh, Aachen (DE)

(72) Inventors: Thorsten Siess, Aachen (DE); Christoph Nix, Aachen (DE); Stefan Bönsch, Aachen (DE)

(73) Assignee: Abiomed Europe Gmbh, Aachen (DE)

( * ) Notice: Subject to any disclaimer, the term of this patent is extended or adjusted under 35 U.S.C. 154(b) by 1246 days.

(21) Appl. No.: 16/959,262

(22) PCT Filed: Jan. 8, 2019

(86) PCT No.: PCT/EP2019/050339
§ 371 (c)(1),
(2) Date: Jun. 30, 2020

(87) PCT Pub. No.: WO2019/137911
PCT Pub. Date: Jul. 18, 2019

(65) Prior Publication Data
US 2020/0360582 A1   Nov. 19, 2020

(30) Foreign Application Priority Data

Jan. 9, 2018 (EP) .................................... 18150702

(51) Int. Cl.
*A61M 60/13* (2021.01)
*A61M 60/139* (2021.01)
(Continued)

(52) U.S. Cl.
CPC .......... *A61M 60/139* (2021.01); *A61M 60/13* (2021.01); *A61M 60/174* (2021.01);
(Continued)

(58) Field of Classification Search
CPC .................................................. A61M 60/546
See application file for complete search history.

(56) References Cited

U.S. PATENT DOCUMENTS

| 7,010,954 B2 | 3/2006 | Siess et al. |
| 2007/0119246 A1 | 5/2007 | Miyakoshi et al. |

(Continued)

FOREIGN PATENT DOCUMENTS

| JP | 2003062065 A | 3/2003 |
| JP | 2005048660 A | 2/2005 |

(Continued)

OTHER PUBLICATIONS

International Search Report dated Apr. 16, 2019 for PCT/EP2019/050339 (11 pages).

(Continued)

*Primary Examiner* — Benjamin J Klein
*Assistant Examiner* — Thien Jason Tran
(74) *Attorney, Agent, or Firm* — Botos Churchill IP Law LLP

(57) ABSTRACT

A method and an apparatus for use in estimating blood flow in an intravascular blood pump comprise retrieving reference data from a set of reference data obtained in a test environment. The set of reference data comprises, for at least one motor speed at different pump loads, including a first pump load, both a reference motor current (I) of a motor driving the blood pump and an amount of fluid flow through the blood pump. After placement of the blood pump in the patient, a patient-specific motor current for said motor speed at said first pump load is measured, and a motor current deviation value ($\Delta I$) is calculated from the reference motor current (I) at said first pump load and patient-specific motor (Continued)

current. Finally, the motor current deviation value ΔI is used for estimating a patient-specific blood flow amount through the blood pump.

20 Claims, 4 Drawing Sheets

(51) Int. Cl.
*A61M 60/174* (2021.01)
*A61M 60/216* (2021.01)
*A61M 60/414* (2021.01)
*A61M 60/538* (2021.01)
*A61M 60/546* (2021.01)
*A61M 60/857* (2021.01)
*A61M 60/865* (2021.01)

(52) U.S. Cl.
CPC ........ *A61M 60/216* (2021.01); *A61M 60/414* (2021.01); *A61M 60/546* (2021.01); *A61M 60/857* (2021.01); *A61M 60/865* (2021.01); *A61M 60/538* (2021.01); *A61M 2205/3334* (2013.01); *A61M 2205/3365* (2013.01); *A61M 2205/3368* (2013.01); *A61M 2205/50* (2013.01); *A61M 2205/702* (2013.01)

(56) References Cited

U.S. PATENT DOCUMENTS

| | | | | |
|---|---|---|---|---|
| 2009/0132184 | A1* | 5/2009 | Miyakoshi | A61M 60/538 702/45 |
| 2010/0130809 | A1* | 5/2010 | Morello | A61M 60/216 600/16 |
| 2012/0029408 | A1* | 2/2012 | Beaudin | A61M 1/369 604/4.01 |
| 2014/0323796 | A1 | 10/2014 | Medvedev et al. | |
| 2016/0038663 | A1* | 2/2016 | Taskin | A61M 60/148 623/3.13 |
| 2018/0078159 | A1* | 3/2018 | Edelman | A61M 60/538 |

FOREIGN PATENT DOCUMENTS

| | | |
|---|---|---|
| JP | 2010119859 A | 6/2010 |
| WO | 2018002271 A1 | 1/2018 |

OTHER PUBLICATIONS

Office Action from corresponding Indian Patent Application No. 202037032379 dated Apr. 7, 2022, (6 pp.).

Office Action from corresponding Chinese Application No. 201980007903.3 dated Oct. 9, 2022 (12 pages).

* cited by examiner

METHOD AND APPARATUS FOR CALIBRATION AND USE IN ESTIMATING BLOOD FLOW IN AN INTRAVASCULAR BLOOD PUMP

CROSS-REFERENCE TO RELATED APPLICATIONS

The present application is a national phase entry under 35 U.S.C. § 371 of International Application No. PCT/EP2019/050339, filed Jan. 8, 2019, published as International Publication No. WO 2019/137911 A1, which claims priority to European Patent Application No. 18150702.1, filed Jan. 9, 2018, the disclosures of which are incorporated herein by reference.

BACKGROUND OF THE INVENTION

The present invention relates to a method and an apparatus for calibration and use in estimating blood flow in an intravascular blood pump. The invention further relates to a computer program product programmed to perform said method.

Intravascular blood pumps are used to support the function of a patient's heart, either as a left ventricular assist device (LVAD) or a right ventricular assist device (RVAD). An intravascular blood pump in context with the present invention typically comprises a catheter and a pumping device attached to the catheter which is percutaneously inserted into the patient's heart, e.g. through the aorta into the left ventricle or through the vena cava into the right ventricle. The catheter may have an elongate body with a proximal portion and a distal portion and may extend along a longitudinal axis, wherein the pumping device is attached to the catheter at the distal portion remote from an operator, such as a surgeon. The pumping device typically comprises a pump section with a blood flow inlet and a blood flow outlet. In order to cause a blood flow from the blood flow inlet e.g. in the left ventricle to the blood flow outlet e.g. in the aorta, typically an impeller or rotor is rotatably supported within a pump casing about an axis of rotation for conveying the blood. The blood pump may be driven by a motor included in the pumping device adjacent to the pump section or may alternatively be driven by a motor outside the patient's body, in which case the motor is connected to the impeller or rotor by a flexible drive shaft, i.e. a drive cable, extending through the catheter, herein referred as cable driven blood pumps.

BRIEF SUMMARY OF THE INVENTION

It is important to estimate the blood flow through the blood pump to provide the medical staff with data from which the medical staff can draw certain conclusions about the functioning of the system and/or the status of the patient. In particular, it is important for the medical staff to ensure that the blood pump always delivers the required blood flow in order to sufficiently support or replace the heart function.

Typically, the blood pump operates at a selected motor speed, i.e. the impeller or rotor is driven at a defined number of revolutions per minute. The motor speed or number of revolutions per minute can be changed as needed. At a given motor speed, the blood flow through the blood pump depends on the pressure difference which the blood pump has to overcome. In the following, the pressure difference will also be referred to as "pump load". Accordingly, the maximum blood flow occurs when there is no pressure difference, whereas the blood flow can be zero or there can even occur backflow through the blood pump if the pressure difference is high, e.g. when the ventricle is starting to fill with blood and the blood pump is pumping blood from the low-pressurized ventricle into the high-pressurized aorta, e.g. during diastole. When the overall pump flow during a cardiac cycle is below the desired amount of blood flow, the motor speed is accordingly increased until the desired amount of blood flow is reached.

In order to estimate the blood flow, it is proposed in U.S. Pat. No. 7,010,954 B2 to provide a look-up table or graph for the blood pump in which for a particular motor speed of the blood pump the blood flow versus the pump load is given. This look-up table or graph is provided for various motor speeds. In this way, using a first pressure sensor placed in the aorta and a second pressure sensor placed in the left ventricle, one can refer to the look-up table or graph for the particular motor speed at which the blood pump is driven and conclude from the measured blood pressure difference the current blood flow through the blood pump.

It has been found that the pump load, i.e. the pressure difference to be overcome by the blood pump, does not only have an influence on the blood flow but to a certain extent also on the motor current required to maintain the given motor speed at the set point, i.e. to keep constant the number of revolutions per minute of the impeller or rotor independent of the pump load.

Accordingly, it is possible to draft a look-up table or graph for each motor speed in which the blood flow is correlated with the motor current. Thus, according to the present invention, rather than monitoring the ventricular and aortic pressures, the motor current is monitored.

Data for use in a look-up table or graph, e.g. such as motor current and blood flow, can be recorded in a test bench assembly by running a pump in a fluid at a given motor speed and at a defined pump load while recording the flow produced by the pump. The pump load can be increased over the time, e.g. from zero load (no pressure difference between blood flow inlet and blood flow outlet, i.e. maximum flow) to maximum load (no pump function, i.e. no flow), while the motor current and blood flow are recorded. It is possible to draft such a look-up table or graph for several different motor speeds. As mentioned, the motor current slightly changes when the pump load and flow change. As motor current, blood flow, pump load and motor speed are measured and recorded during the above-explained procedure in a test bench, it is possible to determine a flow at a given motor speed and pump load based on the motor current.

Depending on the blood pump design and several losses, the motor current may increase or decrease over an increasing flow, respectively over a decreasing pump load. For instance, in certain blood pumps, the motor current increases when the pump load increases or, in other words, an increasing motor current indicates decreasing blood flow. In contrast, in other blood pumps the motor current may decrease when the pump load increases or, in other words, an increasing motor current may indicate increasing blood flow through the pump.

Once a blood pump is implanted into a patient's body, largely unknown losses occur. Several parameters such as motor parameters and pump parameters may influence the relationship between the motor current and the blood flow. In addition, the viscosity of the blood through the pump and/or a purge fluid administered through the catheter into the patient's blood may have an influence. Also, frictional losses may have an influence, in particular friction of a flexible drive shaft inside the catheter of a cable-driven blood pump, wherein such friction may be higher or lower depending on the bending curvatures of the catheter through the patient's vascular system. Consequently, it is not possible to reliably determine the flow based on a measured motor current at a given motor speed once the blood pump is implanted in a patient's body.

Therefore, it is a particular object of the present invention to provide a method and an apparatus for use in estimating blood flow in an intravascular blood pump which help medical staff to monitor blood flow upon operating an intravascular blood pump in a patient's body. It is a further object of the present invention to provide a respective computer program product programmed to implement the method and to operate the corresponding apparatus.

These objects are solved by the features of the independent claims. Preferred embodiments of the invention are specified in the dependent claims.

Accordingly, a method for use in blood flow estimation in an intravascular blood pump is suggested, comprising the steps of
(a) retrieving reference data obtained in a test environment, said data comprising, for at least one motor speed at different pump loads including a first pump load, both a reference motor current of a motor driving the blood pump and an amount of fluid flow through the blood pump,
(b) after placement of the pump in a patient, measuring a patient-specific motor current for the at least one motor speed at said first pump load,
(c) thereafter, calculating a motor current deviation value from the reference motor current at the first pump load and the patient-specific motor current for the at least one motor speed at the first pump load, and
(d) finally, applying the motor current deviation value for estimating a patient-specific blood flow amount through the blood pump.

"Motor speed", "speed level" or "motor speed level" refer to the rotational speed of the motor, which correlates with the rotational speed of the pump's rotor or impeller, and can be specified e.g. in revolutions per minute.

"Pump load" is defined as the pressure difference in the fluid that has to be overcome when pumping fluid through the pump. In other words "pump load" can be understood as the pressure difference between the blood flow inlet and blood flow outlet of the pump. Thus, as mentioned above, when the pump is running at a given motor speed, the flow is maximum at zero pump load and the flow is zero at a maximum pump load.

"Fluid flow", "blood flow", "flow" and "blood flow amount" refer to the volume of fluid or blood being conveyed, for instance through the pumping device, per time unit. Accordingly, the flow can be measured in liter per minute.

"Reference data", such as a reference motor current, refers to data that is obtained in a test environment. Accordingly, for estimating the blood flow through a pump which is placed inside a patient's body, reference data are retrieved, e.g. as a look-up table or graph, which were previously obtained in a test environment.

The test environment may simulate a human vessel or organ and, thus, largely simulate the behavior of the blood pump in the human body upon operation of the blood pump therein to keep deviation values low, such as the motor current deviation value.

The present invention can be particularly suitable with cable-driven intravascular blood pumps. Losses caused by friction of the cable inside the catheter largely increase with the number of bendings and tight-bending radii, which may vary from patient to patient. Thus, deviations of reference motor currents measured in a test environment and corresponding specific motor currents occurring in actual use may vary from patient to patient particularly in cable-driven blood pumps.

Said reference data comprise a reference motor current of the motor driving the pump and an amount of fluid flow generated at that particular reference motor current at a given motor speed. These data are obtained for different pump loads because, for maintaining the given motor speed, the motor current is adjusted upon changes of the pump load and, furthermore, because the fluid flow through the constantly driven pump varies with varying pump load, as explained before. The reference data obtained for a given motor speed and correlated as fluid flow versus motor current is advantageously presented as a look-up table or graph. As stated above, depending on the blood pump design the motor current may increase or decrease over an increasing blood flow, respectively over a decreasing pump load.

Such graph or look-up table may be generated for more than one motor speed, such as 2, 3, 4, 5, 6, 7, 8, 9, 10 or more motor speeds. Motor current and fluid flow value pairs for other motor speeds may be interpolated on the basis of the motor current and fluid flow value pairs of the next higher and next lower motor speeds for which reference data have been obtained. In any case, the motor current and fluid flow value pair obtained at different pump loads for each given motor speed include at least a first motor current and fluid flow value pair for a specific "first" pump load. This is important for the next step where, after placement of the blood pump in the patient, a patient-specific motor current is measured for the respective motor speed at said first pump load. The two motor currents, i.e. the reference motor current and the patient-specific motor current, are comparable with each other because they were taken for the same motor speed at the same pump load, namely the first pump load. Thus, a motor current deviation value can be calculated from the reference motor current and the patient-specific motor current for said motor speed at said specific first pump load, and the same process may be carried out for other pump loads and also for the other motor speeds. These motor current deviation values may subsequently be used in the further process of estimating a patient-specific blood flow amount through the blood pump.

For instance, the motor current deviation value may be used to create a patient-specific set of reference data based on the original set of reference data. As mentioned, the original set of reference data shows the dependency between motor current and fluid flow for different motor speeds in a test environment, e.g. in the form of a graph or look-up table. A motor current deviation value can be applied to all reference motor current values to estimate a blood flow through the blood pump that is implanted in a patient.

When applying the calculated motor current deviation value to the original set of reference data, the graphs or corresponding figures in the look-up table may be shifted by simply adding the calculated motor current deviation values to the original reference motor currents for all fluid flows and all motor speeds so that the fluid flows in the patient-specific set of reference data indicate the actual blood flow through the blood pump placed in the patient.

It may be assumed that the motor current deviation value for one first pump load at one first motor speed is about the same for all pump loads at the first motor speed for which it has been calculated. In consequence, one motor current-deviation value may be calculated per motor speed and added to more than one reference motor current of the original set of reference data for that particular motor speed, most preferably to all reference motor currents of the original set of reference data for that particular motor speed so as to establish a complete patient-specific graph or look-up table for that motor speed.

Furthermore, the same (single) motor current deviation value calculated for one particular motor current may also be added to the reference motor currents in the original set of reference data for other motor speeds than the particular motor speed for which it has been calculated, so that only one single motor current deviation value needs to be calculated overall.

However, more preferably, a single motor current deviation value is calculated individually for each of the motor speeds for which reference data are available in the set of reference data, because in some blood pumps the motor current deviation value may significantly differ between different motor speeds.

Alternatively, rather than building up a patient-specific set of reference data, the one or more single motor current deviation values may be stored as such and may be deducted from any patient-specific motor current being measured in use of the blood pump in the patient. This will likewise result in and provide the medical staff with patient-specific blood flow amounts for the respective motor speed or, if one (single) motor current deviation value is applied to all referenced motor speeds, for all motor speeds.

A critical point is to identify a suitable "first" pump load at which the patient-specific motor current is measured, as it is important to correlate the patient-specific motor current with the corresponding reference motor current at said same "first" pump load.

It is generally possible with the aid of pressure sensors and/or an EKG to identify specific moments in the heart cycle which would allow to correlate the timing of the measured patient-specific motor current at a given motor speed with a corresponding reference motor current in the set of reference data.

However, according to a particularly preferred embodiment of the invention, the patient-specific motor current for determining the motor current deviation value is measured at a pump load which is clearly identifiable by the motor current value so that there is no need for any additional sensors. More specifically, the following is considered: At a given motor speed, maximum blood flow through the pump occurs at minimum load or, in other words, at zero pressure difference between blood flow inlet and blood flow outlet, i.e. when the cardiac valve is open. As will be explained, the open state of the cardiac valve marks a preferred pump load at which the patient-specific motor current for determining the motor current deviation value is measured.

More specifically, in a preferred embodiment, a blood pump is placed in a patient's vessel system in the way that a blood flow inlet is placed in the ventricle, e.g. left ventricle, and the blood flow outlet is placed in a patient's vessel, for example the aorta, wherein the ventricle and vessel are separated by a natural valve, e.g. the aortic valve. Once the valve opens, e.g. during systole, the blood flow inlet and blood flow outlet are pressure-wise no longer separated and, thus, the pressure difference between them is zero. At this point of zero pressure difference between blood flow inlet and blood flow outlet, the blood flow through the pump will be at a maximum level for the selected motor speed and the motor current for that motor speed level will reach either a maximum or a minimum. Accordingly, maximum blood flow for a given motor speed will occur at a minimum or maximum motor current, depending on the design of the blood pump. Thus, depending on the design of a blood pump, either the maximum motor current or the minimum motor current may be taken as an indication of the open state of the cardiac valve, which open state, as mentioned above, marks the preferred pump load at which the patient-specific motor current for determining the motor current deviation value is measured.

It is clear from the set of reference data whether the open state of the cardiac valve (i.e. maximum flow of the blood pump) is identifiable by the maximum motor current value or by the minimum motor current value, namely depending on the inclination of the flow curve in the look-up table or graph. In other words: If the flow curve inclination is negative, the motor current minimum refers to the open stage of the cardiac valve, e.g. aortic valve, and to maximum blood flow, whereas, if the flow curve inclination is positive, the motor current maximum refers to the open stage of the cardiac valve, e.g. aortic valve, and to maximum blood flow.

Thus, the "first pump load" at which the patient-specific motor current is measured is preferably the pump load when the cardiac valve, e.g. the aortic valve, is open.

Accordingly, the step of measuring the patient-specific motor current for the at least one motor speed at said first pump load preferably comprises measuring the maximum or minimum patient-specific motor current for a particular motor speed.

The efficiency of the pump may further be influenced by changing parameters for various, largely unknown reasons while the pump is in the patient. It is therefore preferred to iterate the afore-described method in the sense that after a while the actual motor current deviation value is again calculated against the patient-specific motor current deviation value calculated before. In other words, if the motor current deviation value changes over time as compared to the motor current deviation value previously calculated, then the previously calculated motor current deviation value is replaced with the actual motor current deviation value.

For instance, an actual patient-specific motor current for the at least one motor speed can be measured and a deviation can be calculated from a previously measured patient-specific motor current, which may have been stored as an updated reference motor current. Accordingly, the previously measured patient-specific motor current or previously updated reference motor current can be (further) updated towards the actual patient-specific motor current.

Preferably, the respectively next iteration is triggered by a predefined time interval. This provides the advantage that in case the blood pump is operated for a longer period of time, the motor current can be calibrated such that a specific amount of blood flow is maintained even though specific characteristics of the blood, patient, purge fluid or system have changed. For instance, such time interval may be specified in a range of seconds or minutes or hours or days. The respective time interval may be configured by medical staff.

In addition or in the alternative, a next iteration may be triggered by at least one influencing characteristic, such as a change in motor current, temperature or viscosity of the blood and/or purge fluid or a change of a physical characteristic of the blood pump, such as the motor temperature of the blood pump. Whenever a significant change of one or more of these characteristics is observed, the calculation of the motor current deviation value may be reiterated.

As regards the retrieval of the reference data in the test environment, this is preferably carried out using a blood pump of a certain type and a fluid, wherein the fluid does not necessarily have to be blood. In any case, the fluid is preferably chosen to have a flow behavior which equals the flow behavior of blood. Likewise, it is preferred that the fluid temperature complies with the patient's blood temperature. These measures help to improve the accuracy of the reference data and the comparability thereof with the measured patient-specific data.

According to a particular embodiment, the fluid used in the test environment comprises water and glycerol in a mixing proportion which provides a viscosity equaling the viscosity of blood at a human's body temperature. This provides the advantage that the test fluid can be produced in a straightforward way.

It is further preferred that the blood pump set up in the test environment simulates the curves of the catheter in a human vessel system. In other words: It is preferred that the catheter guiding the blood pump is set up with curvatures in the test bench according to a placement of the blood pump in the human vessel system.

It is of advantage that the method provides method steps that can likewise be implemented as structural features in a respective apparatus for use in estimating blood flow. Such apparatus has structural features which respectively implement corresponding steps of the afore-described method. Accordingly, the features referring to the method and the apparatus can be used interchangeably such that the apparatus performs the proposed method and the proposed method operates the apparatus. Furthermore, the computer program product may accomplish the method and operate the apparatus, for instance when being executed on a computer.

BRIEF DESCRIPTION OF THE DRAWINGS

Further advantages are provided in the context of the accompanying figures which show.

DETAILED DESCRIPTION

Figure 1:
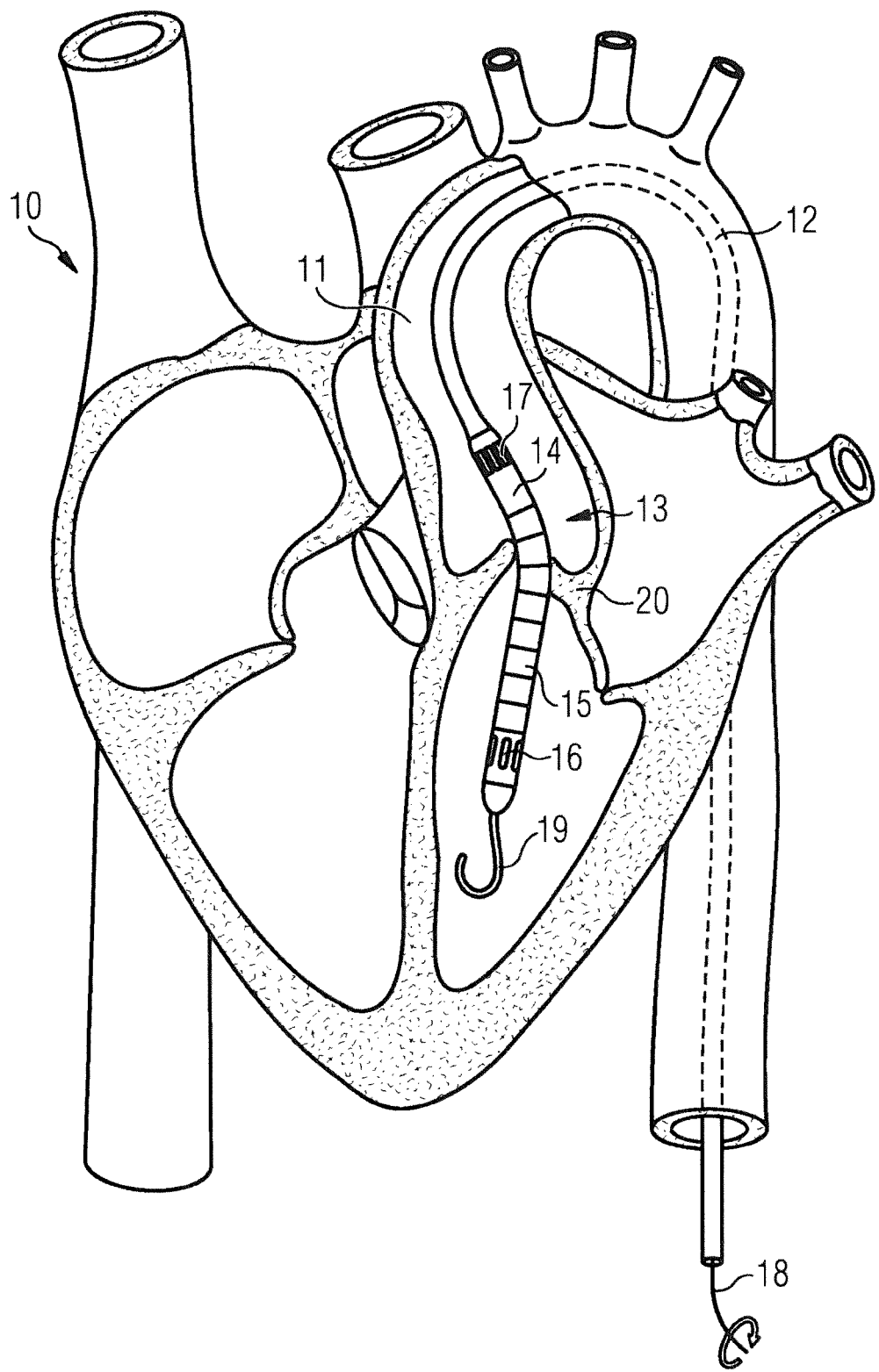
FIG. 1 an intravascular blood pump placed in the left ventricle of a heart.

FIG. 1 shows a human heart 10 into which an intravascular blood pump is inserted through the aorta 11 traversing the aortic valve 20. The intravascular blood pump comprises a catheter 12 and a pumping device 13 attached to the distal end of the catheter 12. The pumping device comprises a pump section 14 and a cannula 15 having inlet openings 16 and outlet openings 17 and further having a soft, flexible tip end 19 in the form of a pigtail which keeps the pumping device 13 away from the heart walls so as to avoid suction of the inlet openings 16 against the heart wall. An impeller or rotor rotates inside the pump section 14 to convey blood from the inlet openings 16 through the outlet opening 17. The pumping device 13 may further comprise a drive section along with the pump section 14 in a single housing for driving the impeller or rotor. However, in the embodiment shown in FIG. 1, the pumping device is driven by a flexible cable 18 which is guided inside the catheter 12. Instead of the pump as shown in FIG. 1, other intravascular blood pumps may be employed, such as expandable blood pumps, the diameter of which would be substantially larger after expansion as compared to the pump section 14 shown in FIG. 1.

Obviously, the drive cable 18 will suffer losses such as surface friction inside the catheter 12 when operated. The amount of losses also depends on the number of bendings and bending radii, which may be different from patient to patient or even for the same patient if the blood pump is relocated or moved inside the patient's vascular system over time. Accordingly, the energy needed to drive the impeller inside the pump section 14 with a given rotational speed may differ according to the individual situation.

Figure 2:
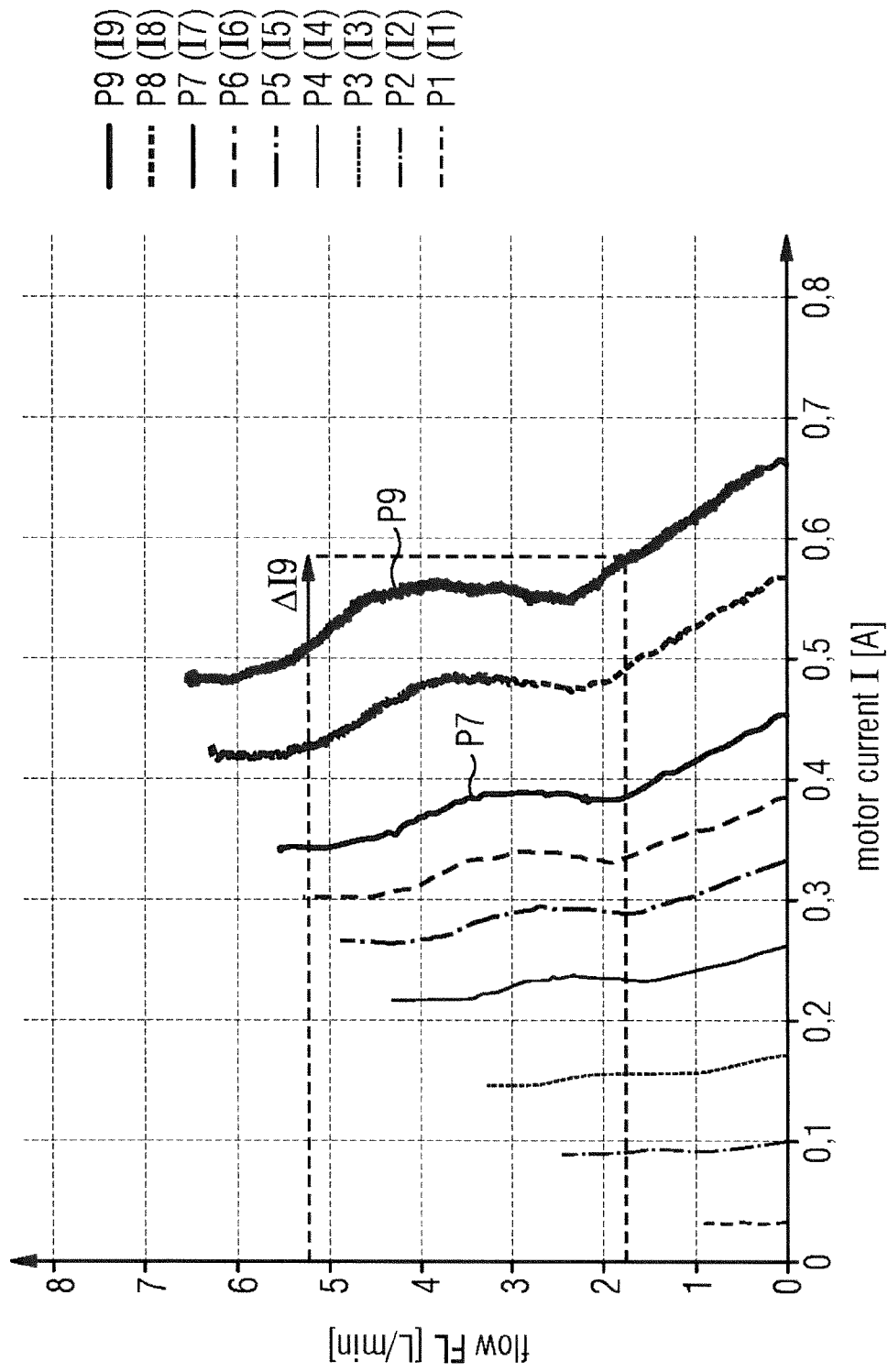
FIG. 2 a graph illustrating a relationship between motor current and fluid flow in a test environment through one exemplary pump for a set of nine different motor speeds.

FIG. 2 shows a diagram with graphs P1 to P9 for the flow FL through the pump in relation to the motor current I for nine different motor speeds N1 to N9, the motor speed N relating to the rotational speed of the impeller. As mentioned before, the higher the pressure difference is which the blood pump has to overcome, the lower the flow FL through the blood pump will be. As can be seen from FIG. 2, the motor current I is not constant for each motor speed N but changes upon a change of the amount of flow FL through the pump. For the particular example shown in FIG. 2, the data were actually recorded from an expandable, cable-driven blood pump. In this case, the motor current I decreases on rising flow FL through the pump. In other blood pumps, in particular in non-expandable blood pumps, it has been found that the motor current I increases on a rising flow FL.

The individual measuring points of the graphs P1 to P9 were obtained by measuring both the blood flow FL through the pump and the motor current I at different pump loads in a test environment. The test environment approximated the conditions in a human body as far as possible. For instance, the fluid in the test environment was chosen to have a flow behavior which equals the flow behavior of blood. Furthermore, the temperature was equal to the patient's blood temperature, such as between 36 and 37° C. Furthermore, the fluid in the test environment comprised water and glycerol in a mixing proportion providing a viscosity which equals the viscosity of blood. Also, the bendings of the catheter and the bending curvatures had been approximated according to a human's average vascular system.

However, since the blood flow FL is estimated based on the motor current I, as suggested herein, rather than based on any pressure signal, the graphs P1 to P9 for the different motor speeds N1 to N9 will have to be calibrated for each individual patient because a deviation of the patient-specific motor current in use of the blood pump inside the patient's heart as compared to the reference motor current I in a corresponding set of reference data may lead to misinterpretations, as will be further explained in connection with FIG. 2.

As shown in FIG. 2, when the blood pump is driven with a motor speed P9 and, because of the pressure difference to be overcome, the blood flow FL is about 5.2 L/min (slightly below the maximum blood flow FL of about 6.5 L/min). When in this situation the patient-specific motor current deviates from the reference motor current I9 by a positive motor current deviation value ΔI9, then the medical staff would erroneously conclude from the set of reference data a blood flow FL of only about 1.8 L/min. Alternatively, when in the same situation the patient-specific motor current deviates from the reference motor current I9 by a negative rather than a positive motor current deviation value −ΔI9

(not shown in FIG. 2), then the medical staff would not find any corresponding reference motor current or the flow estimation system would send an error signal.

Therefore, in order to avoid such misinterpretations, look-up tables or graphs with patient-specific motor current values are generated which the medical staff may refer to and from which the medical staff can conclude the correct blood flow. Accordingly, after placement of the blood pump in the patient, patient-specific motor currents can be measured for the motor speed N9 (and likewise for all other motor speeds) at respective working points of the pump, i.e. at specific pump loads, and corresponding motor current deviation values $\Delta I9$ can be calculated as a difference between the reference motor currents I9 and the measured patient-specific motor currents for these specific pump loads.

Figure 3:
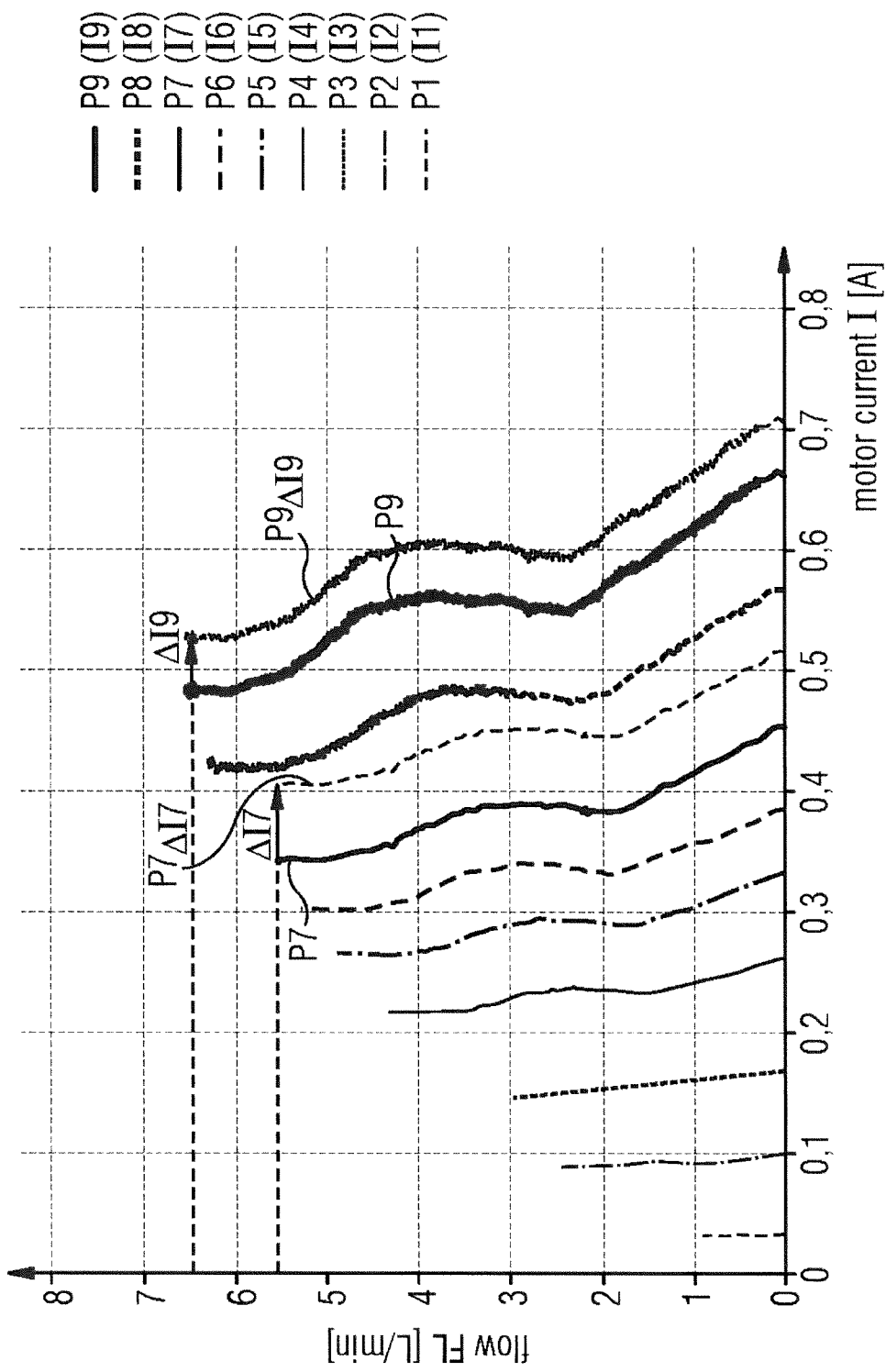
FIG. 3 the graph of FIG. 2 showing additionally two exemplary motor current deviation values ΔI at maximum flow through the pump for two motor speeds.

However, as has been explained above and will be further explained in reference to FIG. 3, the motor current deviation value $\Delta I$ is calculated for only one specific "first" pump load and added to all reference motor currents of a given motor speed N in the set of reference data. And this "first" pump load preferably corresponds to a state of minimum pump load within the cardiac cycle, i.e. an open state of the cardiac valve, because such state can easily be detected solely based on the measured motor current I, namely when the motor current I is either maximum or minimum. However, for the sake of completeness, where pressure sensors and/or an EKG are in place, any other pump load may be taken as the specific "first" pump load at which the motor current deviation value $\Delta I$ is determined.

In any case, either a new set of reference data or an updated set of reference data may be created by adding the calculated motor current deviation value $\Delta I$ to the corresponding reference motor current, and this is done for all pump loads for which reference motor currents are available in the set of reference data so as to obtain a complete patient-specific set of reference data for the motor speed N. Furthermore, this procedure can be carried out for each of the motor speeds N1 to N9 individually.

Even more, assuming that the motor current deviation value $\Delta I9$ obtained at motor speed N9 is approximately identical to the motor current deviation values $\Delta I1 \ldots \Delta I8$ for all other motor speeds N1 to N8, the motor current deviation value $\Delta I9$ may be applied analogously to the sets of reference data for each of the motor speeds N1 to N9.

Alternatively, rather than creating a new or updated set of reference data, respective motor current deviation values $\Delta I$ or $\Delta I1$ to $\Delta I9$ may be stored and deducted from the motor current as measured when the pump is placed inside the patient's vascular system so that the measured motor current is comparable with the set of reference data previously stored.

Most practically, as exemplary shown in FIG. 3 for two motor currents I7 and I9 and their corresponding motor current graphs P7 and P9, single motor current deviation values $\Delta I7$ and $\Delta I9$ are measured at an open state of the cardiac valve, such as the aortic valve in case that the blood pump pumps blood from the left ventricle into the aorta. This moment is easily detectable as it marks the uppermost point in the graphs P1 to P9 shown in FIG. 3, i.e. the points of maximum flow FL. Thus, in the embodiment shown in FIG. 3, the motor current deviation values $\Delta I7$ and $\Delta I9$ of the corresponding patient-specific motor currents as compared to the reference motor currents I7 and I9 are measured when the respective patient-specific motor current reaches its maximum value because this marks the open state or state of maximum flow FL through the blood pump. As shown in FIG. 3, the motor current deviation values $\Delta I7$ and $\Delta I9$ have been applied to all other reference data relating to the corresponding motor speeds I7 and I9, respectively. The new or updated graphs for the motor speeds I7 and I9 are identified in FIG. 3 as $P7_{\Delta I7}$ and $P9_{\Delta I9}$. The same may be carried out for the remaining motor speeds P1 to P6 and P8.

Again, as mentioned above, in certain situations it may be acceptable to calculate one single motor current deviation value $\Delta I$ for one motor speed N and apply this single motor current deviation value also to other motor speeds.

Figure 4:
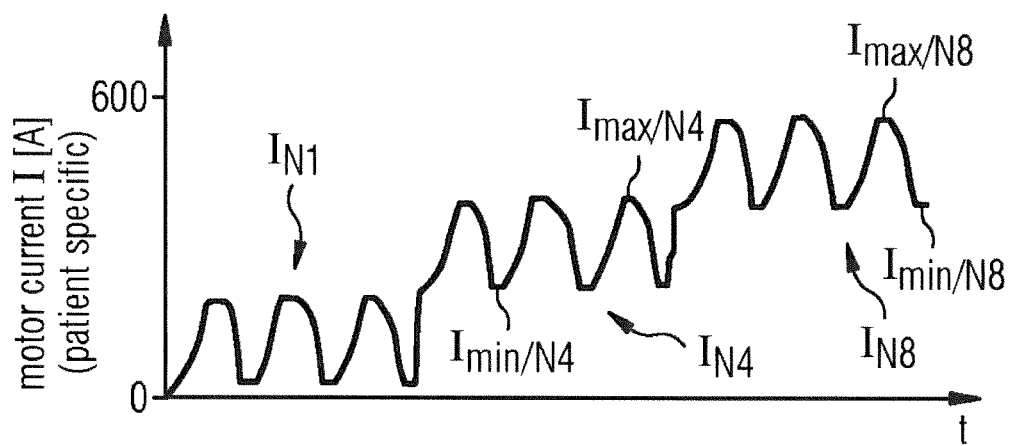
FIG. 4 shows the variation with time of the motor current I over a plurality of heart cycles at different speeds N of a left ventricular pump.

FIG. 4 shows the variation with time of the motor current I over a plurality of heart cycles at different motor speeds N. The curve as shown in FIG. 4 has been obtained after the pump had been placed in a patient's left ventricle. For each motor speed N, three cardiac cycles were monitored and recorded and, as can be seen, the motor current changes over each cardiac cycle in the same characteristic way. In particular, the curve shows a maximum motor current and a minimum motor current for each cycle. Since it is clear from the set of reference data as well as from the negative inclination of the motor current graphs P as shown in FIG. 3 that the minimum motor current corresponds to the state of minimum pump load and maximum flow, this minimum motor current is used as the patient-specific motor current value when calculating the motor current deviation value $\Delta I$ for the corresponding motor speed N. In other blood pumps, where the inclination of the motor current graphs P is positive, it would be the maximum motor current to be used as the patient-specific motor current value for calculating the motor current deviation value $\Delta I$.

Figure 5:
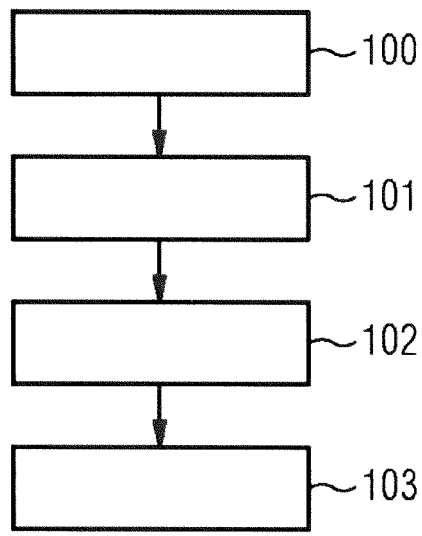
FIG. 5 a flow chart depicting the method for use in estimating blood flow through an intravascular blood pump.

FIG. 5 shows a method of estimating blood flow. In a first step 100, reference data is retrieved from a set of reference data that has been obtained in a test environment. These reference data comprise both a reference motor current I of the motor driving the blood pump and an amount of fluid flow FL through the blood pump for at least one motor speed N (in the example of FIG. 3 for nine motor speeds N1 to N9 as shown in the graphs P1 to P9) at different pump loads, including a "first" pump load which is preferably the minimum pump load at maximum flow FL through the pump, i.e. at an open state of the cardiac valve.

Then, in a second step 101, after placement of the blood pump in the patient, a patient-specific motor current for the respective motor speed N is measured at said "first" pump load, i.e. preferably at minimum pump load and maximum flow. In the example of FIG. 3, it is the minimum patient-specific motor current which is measured as becomes clear from graphs P1 to P9 showing the reference motor currents I1 to I9 that the minimum motor current corresponds to the point of minimum pump load and maximum flow FL.

Thereafter, in step 102, a motor current deviation value $\Delta I$ is calculated by subtracting the measured patient-specific motor current from the corresponding reference motor current I in the set of reference data, i.e. from the reference motor current obtained for said "first" (minimum) pump load at that particular motor speed N.

Finally, in step 103, the motor current deviation value $\Delta I$ is applied to all reference motor currents I of—at least—that particular motor speed N in order to enable a correct estimation of blood flow FL through the blood pump when placed in the patient, as described before.

The skilled person will recognize that the method steps may comprise sub-steps. For instance, as mentioned, the application of the motor current deviation value $\Delta I$ to the reference motor current I may be such that either a new or updated patient-specific look-up table or graph P is created to which the medical staff or the system may refer or that the motor current deviation value ΔI is added to the reference motor current I only at the time of estimation of the blood flow FL by the medical staff or system. Furthermore, the motor current deviation value ΔI measured and calculated for the particular motor speed N may also be applied to all other motor speeds.

In addition, the second step 101 of measuring the patient-specific motor current for the respective motor speed N at said "first" pump load may include the sub-step of monitoring and, preferably, recording the patient-specific motor current over one or preferably more than one complete cardiac cycles at that motor speed N. More preferably, the patient-specific motor current is monitored and, preferably, recorded over one or more complete cardiac cycles at more than only one motor speed N, most preferably at all motor speeds N for which reference motor currents I were obtained in the set of reference data.

The invention claimed is:

1. A method comprising:
   retrieving, from a set of reference data obtained in a test environment, a first reference motor current measured at both a specific motor speed and a specific pump load;
   measuring, after placement of an intravascular blood pump in a patient, at both the specific motor speed and the specific pump load, a first patient-specific motor current drawn by a motor driving the blood pump;
   calculating a motor current deviation value as a difference between (a) the first reference motor current and (b) the first patient-specific motor current;
   calculating an adjusted motor current by applying the calculated motor current deviation value to either (a) a second reference motor current retrieved from the set of reference data or (b) a second patient-specific motor current drawn by the motor driving the blood pump;
   estimating a patient-specific blood flow amount through the blood pump by retrieving, from the set of reference data, an amount of fluid flow corresponding to the adjusted motor current; and
   adjusting a selected motor speed of the motor driving the blood pump based on the estimated patient-specific blood flow amount through the blood pump.

2. The method according to claim 1, wherein applying the calculated motor current deviation value comprises (a) adding the calculated motor current deviation value to the second reference motor current or (b) deducting the calculated motor current deviation value from the second patient-specific motor current.

3. The method according to claim 1, wherein measuring the first patient-specific motor current comprises measuring a maximum or a minimum amount of current drawn by the motor driving the blood pump.

4. The method according claim 1, further comprising updating the calculated motor current deviation value after a predefined time interval.

5. The method according to claim 4, wherein the time interval is configured as a function of at least one influencing characteristic selected from a group of characteristics consisting of: a change in the motor current, a change in a temperature of the blood, a change in a temperature of a purge fluid, a change in a viscosity of the blood, a change in a viscosity of a purge fluid, and a change in a physical characteristic of the blood pump.

6. The method according to claim 1, wherein the set of reference data is obtained in the test environment using a fluid and the blood pump.

7. The method according to claim 6, wherein a temperature of the fluid is between 36° C. and 37° C.

8. The method according to claim 6, wherein the fluid is chosen to have the flow behavior of blood.

9. The method according to claim 6, wherein the fluid comprises water and glycerol in a mixing proportion providing the viscosity of blood.

10. The method according to claim 6, wherein the first reference motor current is obtained in the test environment by measuring, at both the specific motor speed and the specific pump load, an amount of current drawn by the motor driving the blood pump.

11. A system comprising:
    an intravascular blood pump comprising a motor for driving the blood pump; and
    one or more processors configured to:
    retrieve, from a set of reference data obtained in a test environment, a first reference motor current measured at both a specific motor speed and a specific pump load;
    obtain, after placement of the blood pump in a patient, at both the specific motor speed and the specific pump load, a measurement of a first patient-specific motor current drawn by the motor of the blood pump;
    calculate a motor current deviation value as a difference between (a) the first reference motor current and (b) the first patient-specific motor current;
    calculate an adjusted motor current by applying the calculated motor current deviation value to either (a) a second reference motor current retrieved from the set of reference data or (b) a second patient-specific motor current drawn by the motor of the blood pump;
    estimate a patient-specific blood flow amount through the blood pump by retrieving, from the set of reference data, an amount of fluid flow corresponding to the adjusted motor current; and
    adjust a selected motor speed of the motor of the blood pump based on the estimated patient-specific blood flow amount through the blood pump.

12. The system according to claim 11, wherein the blood pump is a cable-driven blood pump.

13. A non-transitory computer readable storage medium having instructions stored thereon that, when executed by one or more processors, cause the one or more processors to:
    retrieve, from a set of reference data obtained in a test environment, a first reference motor current measured at both a specific motor speed and a specific pump load;
    obtain, after placement of an intravascular blood pump in a patient, at both the specific motor speed and the specific pump load, a measurement of a first patient-specific motor current drawn by a motor driving the blood pump;
    calculate a motor current deviation value as a difference between (a) the first reference motor current and (b) the first patient-specific motor current;
    calculate an adjusted motor current by applying the calculated motor current deviation value to either (a) a second reference motor current retrieved from the set of reference data or (b) a second patient-specific motor current drawn by the motor driving the blood pump;
    estimate a patient-specific blood flow amount through the blood pump by retrieving, from the set of reference data, an amount of fluid flow corresponding to the adjusted motor current; and
    adjust a selected motor speed of the motor driving the blood pump based on the estimated patient-specific blood flow amount through the blood pump.

14. The method according to claim 3, wherein measuring the first patient-specific motor current comprises measuring the maximum amount of current drawn by the motor driving the blood pump.

15. The method according to claim 3, wherein measuring the first patient-specific motor current comprises measuring the minimum amount of current drawn by the motor driving the blood pump.

16. The method according to claim 1, wherein the specific pump load is a zero load.

17. The method according to claim 1, wherein the first patient-specific motor current is measured during systole.

18. The system according to claim 11, wherein applying the calculated motor current deviation value comprises (a) adding the calculated motor current deviation value to the second reference motor current or (b) deducting the calculated motor current deviation value from the second patient-specific motor current.

19. The system according to claim 11, wherein the specific pump load is a zero load.

20. The system according to claim 11, wherein the first patient-specific motor current is measured during systole.

\* \* \* \* \*